US006436411B1

(12) United States Patent
Riordan et al.

(10) Patent No.: US 6,436,411 B1
(45) Date of Patent: Aug. 20, 2002

(54) CANCER TREATMENT METHOD

(75) Inventors: Neil H. Riordan, Chandler, AZ (US);
Hugh D. Riordan, Wichita, KS (US)

(73) Assignee: The Center for the Improvement of Human Functioning, Int'l., Inc., Wichita, KS (US)

( * ) Notice: Subject to any disclaimer, the term of this patent is extended or adjusted under 35 U.S.C. 154(b) by 0 days.

(21) Appl. No.: 09/695,701

(22) Filed: Oct. 23, 2000

(51) Int. Cl.$^7$ ............... A01N 1/02; A61K 45/00; A61K 35/12; A61K 35/26; A61K 35/28; C12N 5/00; C12N 5/02; C12N 5/08; C12P 21/04

(52) U.S. Cl. ............... 424/278.1; 424/520; 424/577; 435/2; 435/70.4; 435/372.4; 435/384; 435/405

(58) Field of Search ............... 435/2, 3, 70.4, 435/325, 372.1, 375, 377, 384, 405; 424/198.1, 278.1, 520, 577; 530/351, 380, 399

(56) References Cited

U.S. PATENT DOCUMENTS 4,739,046 A  *  4/1988  Di Luzio
5,128,258 A  *  7/1992  Klostergaard
5,213,970 A  *  5/1993  Lopez-Berestein et al.

OTHER PUBLICATIONS

Abdul et al, "Different effects of interleukin 1 and 2 on cellular proliferation, prostate-specific antigen and chromogranin A levels in prostate cancer cell lines", Proceedings of the American Society for Cancer Research, 1998, vol. 39, p. 112.*

Cameron, "Purified human macrophage secretions suppress tumor growth in the mouse", Journal of the Reticuloendothelial Society, 1983, vol. 34, pp. 45–52.*

Kuo et al, "Increased production of tumor necrosis factor–alpha and release of soluble CD4 and CD8 molecules, but decreased responsiveness to phytohemagglutinin in patients with nasopharyngeal carcinoma", Journal of the Formosan Medical Association, 1994, vol. 93, pp. 223–229 (Abstract).*

Gallo et al, "Interleukin–1 beta and interleukin–6 release by peripheral blood monocytes in head and neck cancer", British Journal of Cancer, 1993, vol. 68, pp. 465–468. (abstract).*

Lorence et al, "In vivo effects of recombinant interferon–gamma", Cancer Letters, 1990, vol. 53, pp. 223–229. (abstract).*

Hesse et al, "Decreased T–lymphocyte migration in patients with malignancy mediated by a suppressor cell population", Journal of Clinical Investigation, 1984, vol. 73, pp. 1078–1085. (abstract).*

* cited by examiner

Primary Examiner—Anthony Caputa
Assistant Examiner—Karen A. Canella
(74) Attorney, Agent, or Firm—Knobbe, Martens, Olson & Bear, LLP

(57) ABSTRACT

Treatment of tumors, including their metastases, is described. Retrieved cytokines and other molecules from the growth medium of human monocytes stimulated ex vivo with gamma globulin, or other immune stimulators are employed for cancer therapy.

22 Claims, No Drawings

CANCER TREATMENT METHOD

FIELD OF THE INVENTION

The invention generally relates to the treatment of cancer, and, more specifically, to the treatment of tumors, including, but not limited to human sarcomas, melanomas, and carcinomas, including their metastases. Specifically it relates to a method for inducing cancer remission through immune stimulation caused by administration of a preparation produced by human monocytes.

BACKGROUND OF THE INVENTION

Therapy for cancer has largely involved the use of radiation, surgery and chemotherapeutic agents. However, results with these treatment modalities, while beneficial in some tumors, has only marginal or no effect in most. Furthermore, these approaches often have unacceptable toxicities. It is generally recognized that a single clonogenic malignant cell can give rise to sufficient progeny to kill the host, and therefore, to successfully treat cancer the entire population of neoplastic cells must be eradicated. This concept implies that if one is to achieve a cure, total excision of a tumor is necessary for a surgical treatment, and complete destruction of all cancer cells is needed for radiation treatment. In practice this is rarely possible and when there are metastases, it is impossible.

The term "chemotherapy" can be defined as the treatment of disease with chemical substances. Used herein chemotherapy refers to application of anti-neoplastic chemicals to an individual with cancer. The goal of chemotherapy is selective toxicity to cancer cells. However, selectivity has been the major problem with chemotherapy agents. The majority of anticancer drugs are indiscriminate at anti-neoplastic concentrations. Typically chemotherapy agents have negative hematological effects (e.g., cessation of mitosis and disintegration of formed elements in marrow and lymphoid tissues), immunosuppressive activity (e.g., depressed white blood cell counts), and negative impacts on epithelial tissues and reproductive tissues, and the nervous system. Chemotherapy can also increase the incidence of secondary cancers.

Immune-stimulating cytokines have been used in, the treatment of cancer. Recombinant interleukin 2 and gamma interferon are now commonly used as adjuvant therapy for renal cell carcinoma. As early as the early 1900's immune therapy for cancer has shown promise. William Coley used a mixed bacterial vaccine in the treatment of sarcomas with mixed success. It is now thought that this mixed bacterial vaccine induced in vivo production of cytokines which were responsible for tumor regression.

In addition to cytokine therapy, other immune-enhancing therapies are currently under investigation. These include dendritic cell therapy, autologous tumor vaccines, genetically altered vaccines, and lymphocytes therapies.

The above immune therapies all have limitations. Recombinant cytokines are effective in a minority of cases. Dendritic cell therapy is time-consuming and expensive and is rarely effective. Autologous tumor vaccines have variable immunogenicity and therefore variable efficacy, and genetically altered vaccines are expensive and are also variably effective.

It is now being recognized that a primary localized immune defect of cancerous tissue is that of reduced ability to adequately present antigen to cytotoxic T cells. Dendritic cells are also known as professional antigen presenting cells and are chiefly responsible for the contextual presentation of antigen to CTLs. It has recently been found that several types of tumor tissue contain dendritic cells in adequate number to perform antigen presentation, however, the intra- and peri-tumoral dendritic cells are immature, and therefore lack the necessary co-stimulatory molecules to effectively present antigen to CTLs. It has also recently been discovered that immature dendritic cells can be forced to mature and become more effective antigen presenting cells by contacting the immature cells with certain cytokines. The most effective preparation of cytokines for inducing dendritic cell maturation is a mixture of cytokines and other unknown molecules found in the growth medium of cultured monocytes exposed to gamma globulin. Herein referred to as monocyte conditioned medium (MCM). Many investigators are currentl using MCM as a maturing agent in human trials of dendritic cell therapy.

Therefore, the need exists for a method of effecting remissions from neoplastic diseases. In particular a method that effects remissions from cancer without causing serious, long-term side effects.

SUMMARY OF THE INVENTION

Of interest was a treatment for cancer which had rapid anti-tumor activity in doses that did not induce intolerable or lasting side effects. A number of substances have been used in the past to activate monocytes or macro,phages and as immune activators. When such substances are administered directly to a patient, they can produce severe side effects. When such substances are administered to macrophages in tissue culture, they induce those cells to produce a number of immune stimulatory molecules including cytokines. The inventors wondered if a preparation composed of the conditioned medium for these cells would be usable as a cancer treatment if administered directly to a patient. It was surprisingly found that monocyte conditioned medium (MCM) when administered to a cancer patient did have anti-neoplastic activity. In addition, A MCM was effective as an antitumor treatment in doses that did not induce intolerable or lasting side effects.

Therefore, the present invention provides a unique solution to the problems with many cancer therapies by providing a therapeutic method for the treatment of cancer by inducing remissions in humans having cancer without serious, long-term side effects. The method in this invention can result in short-term side effects that are clinically manageable. However, the methods do not result in any long-term side effects, in particular immune suppression. The method of this invention will be effective for a broad spectrum of cancerous diseases.

Disclosed is a method for the treatment of cancer in a patient which includes, collecting monocytes from the peripheral blood of the patient or a donor, culturing the monocytes in a culture medium which also contains a macrophage stimulator, collecting the culture medium, and administering the culture medium to a patient. The culture medium can be administered topically, preferably with a transdermal carrier, parenterally, intravenously, peritumorally, and/or intratumorally. The method may also involve concentrating the culture medium, preferably by lyophilization, column chromatography, or filtration. The cancer treatable by this method includes carcinomas, sarcomas, and leukemias and lymphomas and their metastases. In one embodiment, the cancer is squamous cell cancer of the skin, prostate cancer, uterine sarcoma, osteosarcoma, and squamous cell head or neck cancer.

The macrophage stimulator can be a cytokines, bacterial component, or fungal component. Preferably, the macrophage stimulator is gamma-globulin, fungi, fungal cytoplasmic components, fungal cell wall components, bacteria, bacterial cytoplasmic components, bacterial cell wall components, mycoplasma, mycoplasma cytoplasmic components, mycoplasma cell wall components, endotoxins (LPS), muramyl peptides, glucans, Colony Stimulating Factors (CSFs)—GM-CSF or G-CSF, melatonin, lipoproteins, phytohaemagglutinin (PHA), adenosine triphosphate (ATP), ATP metabolites or ATP analogues.

A further aspect of the invention is a pharmaceutical preparation for the treatment of cancer comprising a monocyte-conditioned medium obtained by the method disclosed above.

BRIEF DESCRIPTION OF THE DRAWINGS

FIG. 1 is a graph showing the production of serum PSA (prostate specific antigen) as a function of treatment with MCM.

DETAILED DESCRIPTION OF THE INVENTION

Of interest was a treatment for cancer which had rapid anti-tumor activity in doses that did not induce intolerable or lasting side effects. A number of substances have been used in the past to activate monocytes or macrophages and as immune activators. When such substances are administered directly to a patient, they can produce severe side effects. When such substances are administered to macrophages in tissue culture, they induce those cells to produce a number of immune stimulatory molecules including cytokines. The inventors wondered if a preparation composed of the conditioned medium for these cells would be usable as a cancer treatment if administered directly to a patient. It was surprisingly found that monocyte conditioned medium (MCM) when administered to a cancer patient did have antineoplastic activity. In addition, MCM was effective as an antitumor treatment in doses that did not induce intolerable or lasting side effects.

Therefore, the present invention provides a unique solution to the problems with many cancer therapies by providing a therapeutic method for the treatment of cancer by inducing remissions in humans having cancer without serious, long-term side effects. Although, the method in this invention can result in short-term side effects that are clinically manageable, they do not result in any long-term side effects such as immune suppression. The method of this invention is effective for a broad spectrum of cancerous diseases.

In particular, a novel method for the treatment of cancer is disclosed which involves creating a preparation of cytokines and other molecules by culturing human monocytes in the presence of gamma globulin or other macrophage or immune enhancers, and administering that preparation to a person having cancer. The preparation can be produced from a patient's own monocytes, or alternatively from donor monocytes. Although gamma globulin is known to have a significant immune-stimulating effect, many other substances are known which can also be used. Examples of such substances include but are not restricted to: fungi and fungal cytoplasmic and cell wall components, bacteria and bacterial cytoplasmic and cell wall components, mycoplasma and mycoplasma cytoplasmic and cell wall components, lipopolysaccharide and other endotoxins, muramyl peptides, glucans, Colony Stimulating Factors (G-CSF and GM-CSF), melatonin, lipoproteins, phytohaemagglutinin (PHA), adenosine triphosphate (ATP), ATP metabolites and ATP analogues. Therefore, one or more of these substance can be used in the method of the present invention in place of or in addition to gamma globulin.

The preparation does not always require further processing, purification, or treatment before administration. However, in alternate embodiments, the preparation can be concentrated, further purified, or other pharmaceutically acceptable additives can be added. For example, the pH of the medium may be altered using substances known to one of skill in the art. A toxic, immunologically active, or undesirable substance can be removed before administration of the preparation. A substance can be added which will enhance the effectiveness of the cytokines and other molecules in the conditioned medium preparation. Finally, other chemotherapeutics can be added. Many chemotherapeutics are known to one of skill in the art, but examples include nucleotide analogs, activated immune cells, genetically altered cells which allow recognition of specific tumor antigens, antibodies, peptides, and vectors containing various anti-tumor genes. The amount of immune or macrophage stimulating substance used will vary depending of the substance. The macrophage stimulating activity has been identified for these substances and one of skill in the art would be able to identify an active concentration from those studies.

A number of studies have identified macrophage stimulators and are set out below. Glucans are (1–3)-beta-D-linked polymers of glucose which are produced as fungal cell wall components. Mueller et al (Glycobiology 2000 Apr;10(4):339–46) and Abel, et al (Int J. Immunopharmacol 1992 Nov; 14(8):1363–73) identified that glucans modulate immune function via macrophage participation. Hu et al (J Biol Chem 2000 May 26;275(21):16373–81) identified a number of transcription factors which activated macrophages. These included C/EBPalpha, beta, and delta. Bober et al. compared the ability of GM-CSF and G-CSF to stimulate human monocyte functions in vitro and found them to be equivalent. J. Y. Djeu identified that *C. albicans*, can activate neutrophils (and specifically large granular lymphocytes). Melatonin was found to activate cytokine production by cultured human monocytes (Garcia-Maurino et al. Life Sci 1999;65(20):2143–50). It has long been known that lipopolysaccharide (LPS), an endotoxin from Gram negative bacteria, can activate the immune system. Mackman, et al. (Immunol Res 2000;21(2–3):247–51) also provides evidence that it specifically activates monocytes. Many immune stimulatory components are found in the bacterial cell wall. Examples of these are LPS, the prototypical immune stimulator and muramyl dipeptide (MDP), (Grahames et al. Br. J. Pharmacol 1999 Aug;127(8):1915–21 and Heinzelmann, et al. Immunopharmacology 2000 Jul 20;48(2):117–28). Shiga toxin (Stx) has also been shown to stimulate cytokine synthesis in monocytic cell line in vitro (Foster, et al. Infect Immun 2000 Sep;68(9):5183–9). Although many of the immune stimulatory components of bacteria are found in the cell wall, it was also found that mycoplasma, a bacteria with no cell wall stimulated monocytes and specifically, that *Mycoplasma fermentans*-derived lipoprotein (MALP-2) was a potent inducer of chemokines and cytokines (Kaufmann, et al. Infect Immmun December 1999; 67(12):6303–8). The activity of Phytohaemagglutin (PHA) to stimulate the production of monocytic cytokines was compare to that of LPS and found to be comparable (Le Meur et al. Nephrol Dial Transplant October 1999; 14(10):2420–6). A comparison of LPS with ATP and ATP analogs showed an significant activity on a human monocyte cell line (Grahames, et al. Br J Pharmacol August 1999; 127(8) :1915–21. In addition, to bacteria and fungi, parasites and parasitic components can also stimulate monocytes. Shoda et al. (Infect Immun September 2000; 68(9):5139–45) were able to show monocyte stimulation by *Babesia bovis*, a protozoan. Purified interleukins, thought potentially difficult and expensive to produce can also be used to induce monocyte stimulation. IL-10 (Wolk et al. Pathobiology 1999;67(5–6):253–6) and IL-2 (Pesoa et al. Medicina (B.Aires) 2000;60(2):202–10).

The monocyte conditioned media (MCM) is prepared by treating monocytes in vitro with an immune or macrophage/monocyte-stimulating substance for an amount of time necessary to stimulate the macrophages. The time can vary considerably, because if a shorter time is used, the preparation can be concentrated before use and if a longer time is used, the preparation can be diluted or used as is. Times of from 2 hours to 4 days can be used for a typical macrophage or monocyte culture. In a preferred embodiment, a time of about 1 to 2 days was used. In the case of gamma globulin, the optimal time was the amount of time it took for the monocytes to produce pro-inflammatory substances: (such as TNF and IL-1). Optimally, the time was found to be about 1 to 2 days. After 3–4 days, the amount of anti-inflammatory substances produced makes the preparation less optimal. Approximately 4 hours after treatment with gamma globulin, pro-inflammatory substances were being produced. This means that one option for production of the MCM preparation is to wait a minimum of time and concentrate the MCM from a large number of preparations.

The amount of the immune stimulator added can also vary depending on how the substance is applied to the cells. In one embodiment, the monocyte stimulator is applied to the tissue culture dish, coats it and then the cells are applied. In a further embodiment the monocyte stimulator is applied to the cells before they are plated. In a further embodiment the monocyte stimulator is applied to the cells after they are plated. The immune stimulator can be applied and left on until collection of the culture media or it can be applied and the excess removed.

After incubation, the particulates and cells in the medium may be removed. Removal may be by centrifugation, filtration, or other known methods. Next, the preparation can be further filtered to remove larger or smaller, unwanted molecules. The preparation may also be further purified by chromatography, filtration with smaller pore sized filters, precipitation, and other known methods. Alternatively, the preparation can be concentrated and diluted into a pharmaceutically acceptable solution. However, preferably, the preparation requires very little treatment before administration. This allows for a more cost-effective treatment. Before administration, the solution is sterilized by filtration or other means.

The preparation is administered topically or parenterally, preferably via intravenous, subcutaneous or intra- or peri-tumoral injection, either as a sole agent or in combination with other agents or methods that are commonly used for cancer treatment. This is preferable to the use of gamma globulin intravenously, because gamma globulin given intravenously is "used up" very quickly and will not yield the high concentrations of cytokines produced by our in vitro coculture of moncytes and gamma globulin. This is demonstrated by the fact that intravenous gamma globulin (usually given in multi-gram doses) does not generally result in fever, while our MCM, prepared with as little as 40 mg of gamma globulin does induce cytokine-related effects such as fever, chills, etc.

Preparation of MCM

Preparation of MCM can be accomplished through various methods. All methods require the collection of peripheral monocytes through either a standard venipuncture collection of whole blood, or, preferably collection of peripheral blood mononuclear cells (PBMCs) using an apheresis machine. In the preferred embodiment, an apheresis machine is used to collect the PBMCs from at least 6 liters of blood from a patient or a donor. This type of collection is well known to those skilled in the art.

The collected product containing plasma, lymphocytes, monocytes, and contaminating platelets and red blood cells is then taken to a sterile environment such as a laminar flow hood for processing. The monocytes are then separated from the other materials by centrifugation, antibody selection, selective adherence, or combinations of those methods. In the preferred embodiment monocytes are separated from the other components by first placing the apheresis product in a tube containing a density gradient solution such as Ficoll Paque™, or in commercially available centrifuge tubes already containing a density gradient such as Lymphoprep™ (Gibco, Grand Island, N.Y.) blood cell separation tubes. The tubes are centrifuged according to the manufacturer's specifications, which yields a banded layer of lymphocytes, monocytes, and contaminating platelets and red blood cells. This layer is then removed and resuspended in a culture medium, preferably a serum-free culture medium, and most preferably RPMI 1640 culture medium (Sigma Chemicals, St. Louis, Mo.) containing 1–10% autologous serum in the case of autologous production, or proven, virus free, heat inactivated human serum in the case of donor production.

This mixture of culture medium, lymphocytes, monocytes, and contaminating platelets and red blood cells is then placed in sterile tissue culture flasks or plates. Most preferably plastic tissue culture flasks. The concentration of cells can vary from $1\times10^6$ to $1\times10^8$ cells. The preferred concentration of monocytes for maximal cytokine production is $2\times10^6$ to $4\times10^7$ monocytes per 75 cm$^2$ flask containing 10 mL of culture medium. The most preferred concentration of monocytes for maximal cytokine production is $1\times10^7$ to $3\times10^7$ ($1\times10^6$ to $3\times10^6$ monocytes per mL of culture medium) monocytes per 75 cm$^2$ flask containing 10 mL of culture medium. The mixture is then contacted with human gamma globulin. The gamma globulin can be added directly to the mixture, or, more preferably is coated onto the culture flasks or plates prior to the addition of the cells and culture medium. In the preferred embodiment, four mL of human gamma globulin solution (10 mg/mL) are placed into plastic, sterile 75 cm$^2$ culture flasks. The gamma globulin is left in the flasks for several minutes and then removed prior to the addition of the culture medium, lymphocytes, monocytes, and contaminating platelets and red blood cells. However, other embodiments involved the treatment of monocytes which were already attached to the cells and either removal of the excess gamma globulin so that the cells were "coated", or the gamma globulin can be left without substantial damage to the cells. The concentration of gamma globulin can vary from 0.1 mg/mL to 1000 mg/mL, preferably 1 mg/mL to 100 mg/ml and more preferably 2 mg/mL to 20 mg/mL.

If a different monocyte or immune stimulator is used, one of skill in the art can identify the concentration used in the literature and vary that amount to produce the optimum amount of cytokines and other immuno-stimulatory molecules. For example, it was found that 10 mg/mL of gamma globulin produced an optimum amount of cytokines after 1 to 2 days. One of skill in the art could compare concentrations set out in the literature and identify like concentrations for other immune/monocyte stimulators. For example, in Grahames et al (Br J Pharmacol 1999 Aug;127(8):1915–21) a minimal effective concentration of 1 mM ATP caused release of interleukin 1beta. Therefore, one of skill in the art would use 0.01 to 100 mM ATP, preferably 0.1 to 10 mM ATP, even more preferably 0.8 to 4 mM ATP.

The flasks are then incubated for two hours at 37° C. in a humidified, 5% carbon dioxide/95% air incubator to allow for attachment of the monocytes. The RPMI and 1–10% autologous solution containing most of the contaminating, floating lymphocytes, red blood cells and platelets is then removed from each of the flasks and replaced with fresh RPMI and 1–10% autologous serum. The flasks are then incubated for 1 to 2 days. The culture medium, monocyte conditioned medium, or MCM is removed at that time and sterile filtered. This solution can be used directly as an anti-tumor agent as an additive to a topical solution, or as an injectable. Alternatively, the MCM can be concentrated and purified prior to use by methods known to those skilled in the art and include, but are not limited to: concentration using a molecular weight filter such as an Amicon 3000 Stir Cell to reduce the volume and at the same time remove low molecular weight salts; or, concentration of active components of the MCM using column chromatography; or, lyophilization to remove the water in the medium, effectively concentrating the effective components. These concentrates of MCM can then be re-mixed with a suitable solution and administered as above, either topically, or parenterally.

The concentrations of cytokines in MCM can vary tremendously based on the condition of the donor at the time of harvest. Therefore it may be necessary to titrate the dose of MCM, regardless of the route of administration, to determine the maximum tolerated dose for each recipient. The first side effect normally seen when the maximum tolerated dose is achieved is cooling of the extremities, sometimes associated with headache and backache, followed by shaking, chills, and then fever. These symptoms usually abate within one hour of starting. If the symptoms are severe, oral acetaminophen or ibuprofen or aspirin, and/or intravenous steroid solutions can be given to more rapidly resolve the side effects.

Selected embodiments of the invention are illustrated in Examples 1–6 below:

EXAMPLES OF MCM's EFFICACY AS AN ANTI-TUMOR AGENT

Example 1

A 42 year-old female was treated with MCM. She was diagnosed by tissue pathology with squamous carcinoma of the tongue that metastasized to her right anterior cervical lymph nodes at age 40. At that time she was treated with an electrical treatment (Galvano therapy). She did not receive chemotherapy or radiation at any point. After the electrical treatment her cancer went into remission with negative malignant findings on fine needle aspiration, of the lymph nodes. She presented to the inventors two years after the original diagnosis with swelling of one right anterior cervical lymph node (30 mm), and a large, erythematous mass at the base of the right tongue which displaced the midline of the oropharynx. A fine needle biopsy of the swollen cervical lymph node was determined by pathology to contain squamous carcinoma cells.

After informed consent the patient was connected to a Cobe Spectra™ apheresis machine that was set up for a peripheral blood stem cell collection. Six liters of blood were processed and approximately 1.2 billion mononuclear cells were recovered. Additionally 80 cc of whole blood was collected in serum clot tubes. The serum was separated from these tubes via centrifugation and aseptically transferred to a sterile tube for later use. The mononuclear cells from the apheresis were further purified using Lymphoprep™ (Gibco, Grand Island, N.Y.) blood cell separation tubes. The tubes were centrifuged according to the manufacturer's specifications, which yielded a banded layer of mononuclear cells that included lymphocytes, monocytes, and contaminating platelets and red blood cells. This banded layer was then aspirated and resuspended in RPMI 1640 culture medium (Sigma Chemicals, St. Louis, Mo.) containing 1–10% autologous serum from the serum tubes. Four mL each of human gamma globulin solution (10 mg/mL) were placed into plastic, sterile 100 centimeter in diameter Petri dishes. The gamma globulin was left in the dishes for 10 minutes and then removed. 10 cc of the RPMI with autologous serum solution containing lymphocytes, monocytes, and contaminating platelets and red blood cells were placed into the petri dishes. The dishes were incubated for two hours at 37° C. in a humidified, 5% carbon dioxide/95% air incubator to allow for attachment of the monocytes. The final concentration of monocytes was $3 \times 10^7$ cells per 10 mL of culture medium. The RPMI and 10% autologous solution containing most of the contaminating, floating lymphocytes, red blood cells, and platelets was then removed from each of the Petri dishes and replaced with fresh RPMI and 10% autologous serum. The Petri dishes were then incubated for 48 hours. The solution in which the monocytes were cultured, the MCM, was aspirated and sterile filtered using a 0.2 micron syringe filter. This filtered solution was then concentrated using an Amicon 3000 Dalton membrane filter to remove salts and low molecular weight components from the solution and to concentrate the effective components. The retentate of this solution was then resuspended in phosphate buffered saline, and lyophilized. The lyophilized powder was resuspended in a sterile saline for injection solution at various concentrations. The concentration of cytokines in the solution was arbitrarily assigned a value based on the number of monocytes used in their production. One unit of MCM was the product of one million starting monocytes.

Treatment

After informed consent the patient was injected with 1–3 units of MCM every other day for 3 weeks. The MCM was alternatingly injected intravenously, intra-tumorally, and peritumorally. After 3 weeks, the lymph node that was originally 30 mm in diameter was reduce in size to 10 mm, and the erythematous mass at the base of the tongue was no longer palpable, or erythematous and no longer displaced the midline of the oropharynx.

Example 2

A 74 year old male was seen by the inventors. He was previously diagnosed with squamous carcinoma in situ of the skin. Upon examination, two scaly, erythematous, raised lesions with marginated borders consistent with squamous cell carcinoma were appreciated on the torso. One measuring 12 mm in its greatest dimension was on the skin at the costal border at the right mid-clavicular line; the other measuring 8 mm in its greatest dimension was on the lower left abdomen, 8 cm inferior and lateral to the navel. The patient was scheduled for surgical removal of the lesions. After informed consent and before the scheduled surgery the patient was treated using the following method.

MCM Preparation 10 cc of whole blood was removed from the patient from an antecubital vein and collected in a serum clot tube. The serum was separated via centrifugation and aseptically transferred to a sterile tube for later use. Additionally, 100 cc of whole blood was removed from an antecubital vein and collected in standard heparinized, glass blood collection tubes. The heparinized whole blood was then layered onto Lymphoprep™ (Gibco, Grand Island, N.Y.) blood cell separation tubes. The tubes were centrifuged according to the manufacturer's specifications, which yielded a banded layer of mononuclear cells that included lymphocytes, monocytes, and contaminating platelets and red blood cells. This layer was then removed and resuspended in RPMI 1640 culture medium (Sigma Chemicals, St. Louis, Mo.) containing 10% autologous serum from the serum tube to yield a final volume of 20 mL. Four mL each of human gamma globulin solution (10 mg/mL) were placed into two plastic, sterile 100 centimeter in diameter Petri dishes. The gamma globulin was left in the dishes for 10 minutes and then removed. 10 cc of the RPMI with autologous serum solution containing lymphocytes, monocytes, and contaminating platelets were placed into each of the petri dishes. The dishes were incubated for two hours at 37° C. in a humidified, 5% carbon dioxide/95% air incubator to allow for attachment of the monocytes. The RPMI and 10% autologous solution containing floating contaminating lymphocytes, red blood cells and platelet was then removed from each of the Petri dishes and replaced with fresh RPMI and 10% autologous serum. The Petri dishes were then incubated further. The final concentration of monocytes was approximately $2\times10^7$ cells per 10 mL of culture medium. After 2 days, the Petri dishes were removed from the incubator. The solution in which the monocytes were cultured (MCM) was aspirated and sterile filtered using a 0.2 micron syringe filter. This filtered solution was then concentrated using an Amicon 3000 Dalton membrane filter to remove salts and low molecular weight components from the solution. The retentate of this solution was then resuspended in phosphate buffered saline, and lyophilized. The lyophilized powder was resuspended in 10 cc of a solution containing 40% dimethyl sulfoxide (as a transdermal carrier) and 60% normal 3 saline to yield 10 cc of treatment solution.

Treatment

Approximately 0.2 cc of the treatment solution was placed onto the larger lesion located at the costal margin. at the mid-clavicular line, 2 times per day for 25 days. After 7 days 4 erythematous foci within the tumor were appreciable, and subsequently, in succession, these foci disappeared over the following 3 weeks. At that time the treated lesion was smooth to the touch, mildly erythematous, non-raised, and without clearly demarcated margins. Upon examination of the other lesion that was not treated it was found to also be smooth to the touch, non-erythematous, non-raised, and smaller is size. Six months after treatment the untreated lesion was not visible and the treated lesion was smooth, similar in size, non-erythematous, and mildly discolored compared to surrounding skin. Upon examination neither lesion was characteristic of squamous cell carcinoma in situ.

Example 3

A 69 year old male with tissue diagnosed prostate cancer was treated with intravenous MCM. His PSA was elevated prior to treatment at 128 ng/mL.

After informed consent the patient was connected to a Cobe Spectra™ apheresis machine that was set up for a peripheral blood stem cell collection. Six liters of blood were processed and approximately 1.0 billion mononuclear cells were recovered. Additionally 80 cc of whole blood was collected in serum clot tubes. The serum was separated from these tubes via centrifugation and aseptically transferred to a sterile tube for later use. The mononuclear cells from the apheresis were further purified using Lymphoprep™ (Gibco, Grand Island, N.Y.) blood cell separation tubes. The tubes were centrifuged according to the manufacturer's specifications, which yielded a banded layer of mononuclear cells that included lymphocytes, monocytes, and contaminating platelets and red blood cells. This banded layer was then aspirated and resuspended in RPMI 1640 culture medium (Sigma Chemicals, St. Louis, Mo.) containing 10% autologous serum from $_1$the serum tubes. Four mL each of human gamma globulin solution (10 mg/mL) were placed into plastic, sterile 100 centimeter in diameter Petri dishes. The gamma globulin was left in the dishes for 10 minutes and then removed. 10 cc of the RPMI with autologous serum solution containing lymphocytes, monocytes, and contaminating platelets and red blood cells were placed into the petri dishes. The dishes were incubated for two hours at 37° C. in a humidified, 5% carbon dioxide/95% air incubator to allow for attachment of the monocytes. The final concentration of monocytes was $3\times10^7$ cells per 10 mL of culture medium. The RPMI and 10% autologous solution containing most of the contaminating, floating lymphocytes, red blood cells, and platelets was then removed from each of the Petri dishes and replaced with fresh RPMI and 10% autologous serum. The Petri dishes were then incubated for 48 hours. The solution in which the monocytes were cultured (MCM) was aspirated and sterile filtered using a 0.2 micron syringe filter. This filtered solution was then concentrated using an Amicon 3000 Dalton membrane filter to remove salts and low molecular weight components from the solution and to concentrate the effective components. The retentate of this solution was then resuspended in phosphate buffered saline, and lyophilized. The lyophilized powder was resuspended in a sterile saline for injection solution at various concentrations. The concentration of cytokines in the solution was arbitrarily assigned a value based on the number of monocytes used in their production. One unit of monocyte conditioned medium was the product of one million starting monocytes.

After informed consent the patient was given daily intravenous injections of MCM diluted in 100 mL of normal saline, starting on day one with a dose of two units. On subsequent days, the MCM dose was increased to 4, 8, 16, 25, and 37.5 units respectively. The patient tolerated the infusions well. Approximately 1 hour after receiving the 8-unit dose of MCM, his sclerae were moderately erythematous. This cleared within ½ hour. After receiving the 25-unit dose of MCM, he reported slight achiness in his joints, and tingling in his hands and upper legs, which abated within ½ hour. After receiving approximately 75% of the 37.5 unit dose of MCM he began to shake, sweat, and complain of chills. The MCM was stopped at that time. His temperature went up to a high of 38.3° C. He was given 1000 mg of Panadol (Tylenol) by mouth. He said he felt better almost immediately, and all signs of shaking disappeared within 45 minutes. One hour after cessation of therapy his blood pressure and pulse were normal and close to baseline and his temperature was down to 37.4. FIG. 1 shows a graph of this patient's PSA before, during and after treatment. The figure also shows a predicted PSA curve based on his pre-treatment PSA levels. The patient's PSA dropped to levels below the predicted concentration based on rate of rise of previous, serial, serum PSA measurements—consistent with accepted objective response prostate cancer treatment criteria. At 6 monthly follow-ups the patients white blood count, chemistry profiles, and urinalyses were all normal.

This example demonstrates several things. The first is that the MCM treatment resulted in a rapid, unexpected rise in serum PSA concentrations that can only be explained two ways: A. There was a rapid increase in tumor burden, as serum PSA concentrations closely correlate with tumor burden; or B. There was rapid tumor cell death induced by the MCM which resulted in a release of PSA from lysed, dead, dying, or apoptotic prostate cells into the serum, similar to what is seen after laser ablation of the prostate. Given the objective response seen during the subsequent drop in serum PSA values, the former hypothesis—that tumor cells died in response to the therapy is the only viable explanation for the rise in PSA. The second point this case demonstrates is that the symptoms of a maximum tolerable dose of MCM are tolerable, easily manageable and abate quickly. This case also demonstrates that the treatment did not result in the type of immunosuppression normally found in cancer treatments, as the patient's white blood count remained normal in the six months following treatment. The final point this case demonstrates is that, due to the rapid effects of the MCM on the serum PSA concentrations, the suspected tumor cell lysis that unexpectantly occurred must have taken place due to a mechanism separate from the hypothesized induction of dendritic cell maturation, due to the long period of time (several weeks to months) required to induce an anti-tumor response via that mechanism.

Example 4

A 52 year old female patient with documented uterine sarcoma with multiple metastases to the lungs was treated with MCM. The lung metastases were diagnosed 4.5 years before treatment began. She had received previous chemotherapy and radiation which did not resolve the lung tumors.

After informed consent was obtained, peripheral blood mononuclear cells were harvested from the patient using a Cobe Apheresis Machine. The cells were immediately taken to the laboratory, where they were placed in culture medium as follows:

Approximately 50 million autologous monocyte cells each were placed in each of 10, 100 mm petri dishes which had been coated with 4 mL fresh human gamma globulin (10 mg/mL) and contained 8 cc of OptiMem culture medium. MCM was prepared by harvesting the medium for the MCM dishes on day 2 of culture, and passing the medium through a 3000 Dalton membrane. The retentate was normalized as 1 unit per one million monocyte cells used in production per mL in sterile normal saline and sterile filtered.

After informed consent was obtained, an infusion of 10 units MCM in 100 cc normal saline, IV over 1 hour, was begun. After 2.5 units had been administered, the patient became short of breath, had distal cyanosis, and pulse oximeter showed a pulse ox of 71%. She was placed on 4 L of oxygen by mask which resolved the cyanosis. She was given 600 mg of paracetamol by mouth, and 4 mg dexamethasone IV. Another 8 mg of dexamethasone was infused 30 minutes later. Within one hour the patient's pulse oximeter concentration was was 98% on 4 liters of oxygen and 92% on room air. The patient received no further MCM treatment. One month after the single treatment a chest x-ray revealed no tumors in the lung fields.

Example 5

A 26 year old with a large primary abdominal osteosarcoma was treated with MCM. After informed consent was obtained, peripheral blood mononuclear cells were harvested from a donor screened for infectious diseases using a Cobe Apheresis Machine. The cells were immediately taken to the laboratory, where they were placed in culture medium as follows:

Approximatley 50 million autologous monocyte cells each were placed in each of 10, 100 mm petri dishes which had been coated with 4 mL fresh human gamma globulin (10 mg/mL) and contained 8 cc of OptiMem culture medium. MCM was prepared by harvesting the medium for the MCM dishes on day 2 of culture, and passing the medium through a 3000 Dalton membrane. The retentate was normalized as 1 unit per one million monocyte cells used in production per mL in sterile normal saline and sterile filtered.

After informed consent was obtained, an infusion of 25 units MCM in 100 cc normal saline, IV over 1 hour, was given. This dosage was tolerated well. MCM was administered in the same fashion as above every weekday, increasing the dose by 5 units per day until a daily dosage of 100 units was reached. The patient had transient flu-like symptoms after each 100 unit dose of MCM that were managed using anti-inflammatory medications. After the fourth administration of 100 units of MCM, the patient began experiencing elevated serum creatinine levels and was hospitalized. At that point a shunt was placed into the tumor. The shunt drained more than 1000 mL of dark fluid. Cytology of the fluid revealed necrotic tumor cells. A CT Scan one month after placement of the drain revealed a significant reduction in the tumor mass size.

Although the present invention has been described in terms of certain preferred embodiments, other embodiments of the invention will become apparent to those of skill in the art in view of the disclosure herein. Thus, obvious changes and modifications may be made without departing from the spirit and scope of the invention. Accordingly, The scope of the invention is not intended to be limited by the foregoing, but rather to be defined only by the claims which follow.

What is claimed is:

1. A method for the treatment of cancer in a patient, comprising:

collecting monocytes from the peripheral blood of the patient or a donor;

culturing said monocytes in a vessel pre-treated with gamma-globulin at a concentration from 10 mg/ml to 1000 mg/ml for a time sufficient to stimulate the macrophages or monocytes to produce TNFα;

separating macrophages and monocytes from the culture medium collecting said culture medium; and administering said culture medium to said patient.

2. The method of claim 1, wherein said culture medium is administered topically.

3. The method of claim 1, wherein said culture medium is applied topically in a solution comprising a transdermal carrier.

4. The method of claim 1, wherein said culture medium is administered parenterally.

5. The method of claim 1, wherein said culture medium is administered intravenously.

6. The method of claim 1, wherein said culture medium is administered peritumorally.

7. The method of claim 1, wherein said culture medium is administered intratumorally.

8. The method of claim 1, further comprising concentrating said culture medium.

9. The method of claim 7, wherein said concentration is by lyophilization.

10. The method of claim 7, wherein said concentration is by column chromatography.

11. The method of claim 7, wherein said concentration is by filtration.

12. The method of claim 1, wherein said cancer is selected from the group consisting of carcinomas, sarcomas, and leukemias and lymphomas.

13. The method of claim 1, wherein said cancer is selected from the group consisting of: squamous cell cancer of the skin, prostate cancer, uterine sarcoma, osteosarcoma, and squamous cell head and neck cancer.

14. The method of claim 1, wherein said macrophage/monocyte stimulator comprises a substance selected from the group consisting of: cytokines, bacterial components, and fungal components.

15. The method of claim 1, wherein said macrophage/monocyte stimulator is selected from the group consisting of: gamma-globulin, fungi, fungal cytoplasmic components, fungal cell wall components, bacteria, bacterial cytoplasmic components, bacterial cell wall components, mycoplasma, mycoplasma cytoplasmic components, mycoplasma cell wall components, endotoxins, muramyl: peptides, glucans, Colony Stimulating Factors (CSFs), melatonin, lipoproteins, phytohaemagglutinin (PHA), adenosine triphosphate (ATP), ATP metabolites and ATP analogues.

16. The method of claim 13, wherein said Colony Stimulating Factors are G-CSF or GM-CSF.

17. The method of claim 13, wherein said endotoxins are lipopolysaccharides.

18. The method of claim 1, wherein said macrophage/monocyte stimulator is gamma-globulin.

19. The method of claim 1, wherein said macrophage/monocyte stimulator added before the cells are plated.

20. The method of claim 1, wherein said macrophage/monocyte stimulator is added after the cells are plated.

21. The method of claim 17, wherein the macrophage/monocyte stimulator is added to a tissue culture plate, allowed to coat the plate and then the cells are plated.

22. The method of claim 1, wherein the macrophage/monocyte stimulator is added to the cells, allowed to coat them and then the excess is removed.

* * * * *